US00PP09323P

United States Patent [19]

van der Knaap

[11] Patent Number: Plant 9,323

[45] Date of Patent: Oct. 10, 1995

[54] *FICUS LYRATA* PLANT NAMED 'BAMBINO+2

[76] Inventor: Eduard J. M. van der Knaap, Wilgenlei 15, 2665 KN Bleiswijk, Netherlands

[21] Appl. No.: 354,143

[22] Filed: Dec. 6, 1994

[51] Int. Cl.[6] ..... A01H 5/00

[52] U.S. Cl. ..... Plt./88.9

[58] Field of Search ..... Plt./33.1, 88.9

*Primary Examiner*—James R. Feyrer

*Attorney, Agent, or Firm*—Burns, Doane, Swecker & Mathis

[57] ABSTRACT

A new and distinct *Ficus lyrata* cultivar named Bambino is provided that is well suited for growing in pots as an attractive foliage plant. The growth habit of the new cultivar is extremely compact. The leaves are uniformly green with light venation and lack variegation. The leaves also are smaller and thicker than those commonly exhibited by *Ficus lyrata.* Additionally, the petioles are extremely short when compared to those commonly exhibited by *Ficus lyrata.*

2 Drawing Sheets

SUMMARY OF THE INVENTION

The present invention comprises a new and distinct Fiddle-Leaf Fig cultivar name Bambino.

*Ficus lyrata* plants frequently are potted and are grown as ornamental foliage plants. Commonly, such plants are not sold by cultivar designation; however, *Ficus lyrata* plants of the Full Speed and Goldy cultivars are established and known to the horticultural industry of The Netherlands. Neither of these previously-recognized cultivars is the subject of a United States Plant Patent. The Full Speed cultivar is very similar in appearance to plants commonly sold under the species designation and is fast growing and possesses the large fiddle-shaped leaves that are typical of the species. The Goldy cultivar is similarly large-leafed; however, the leaf coloration is variegated.

The new Bambino cultivar of the present invention was discovered during 1992 as a whole plant mutation of unknown causation growing among *Ficus lyrata* plants present in the greenhouses of the De Wilgenlei pot-plant nursery located at Bleiswijk, The Netherlands. Had the new Bambino cultivar not been discovered, recognized for its distinctiveness, and carefully preserved, it would have been lost to mankind.

It was found that the new cultivar of the present invention possesses the following combination of characteristics:

(a) exhibits an extremely compact growth habit unlike that typically exhibited by *Ficus lyrata,*

(b) forms uniformly green leaves with light venation, (c) forms smaller and thicker leaves than are typically exhibited by *Ficus lyrata,* and (d) forms extremely short petioles that commonly are considerably longer in *Ficus lyrata.*

Asexual reproduction of the new Bambino cultivar has been accomplished by the use of vegetative cuttings in a controlled greenhouse environment at Bleiswijk, The Netherlands. Horticultural examination of plants resulting from such asexual propagation has demonstrated that the unique combination of characteristics as herein described for the Bambino cultivar is firmly fixed and is retained through successive generations of such reproduction.

BRIEF DESCRIPTION OF PHOTOGRAPHS

The accompanying photographs show typical characteristics of the new Bambino cultivar with colors being as nearly true as it is reasonably possible to make the same in color illustrations of this character. The plants were grown in greenhouses at Bleiswijk, The Netherlands.

Figure 1:
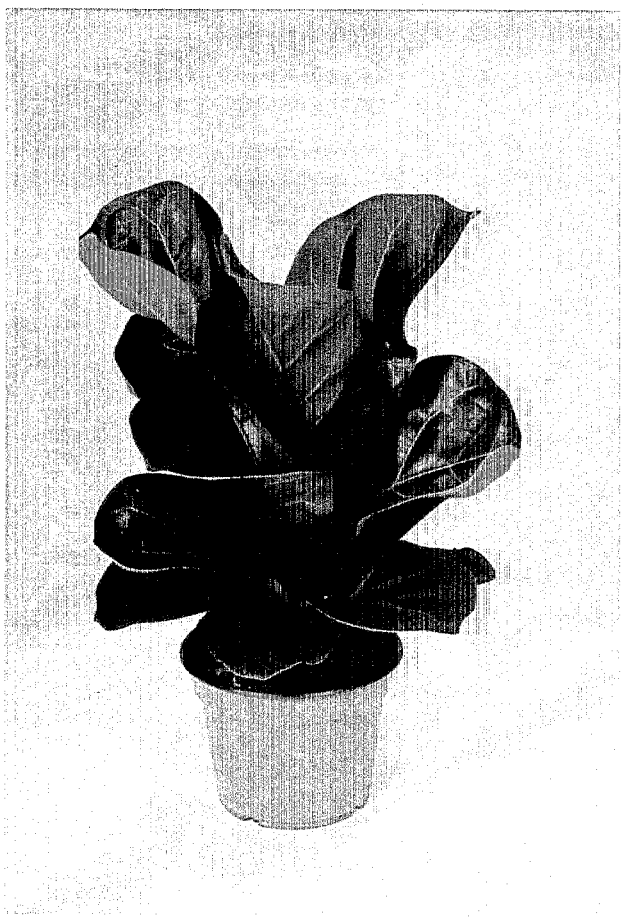
FIG. 1 illustrates a typical potted plant of the Bambino cultivar wherein the attractive glossy foliage and extremely compact growth habit are apparent.
Figure 2:
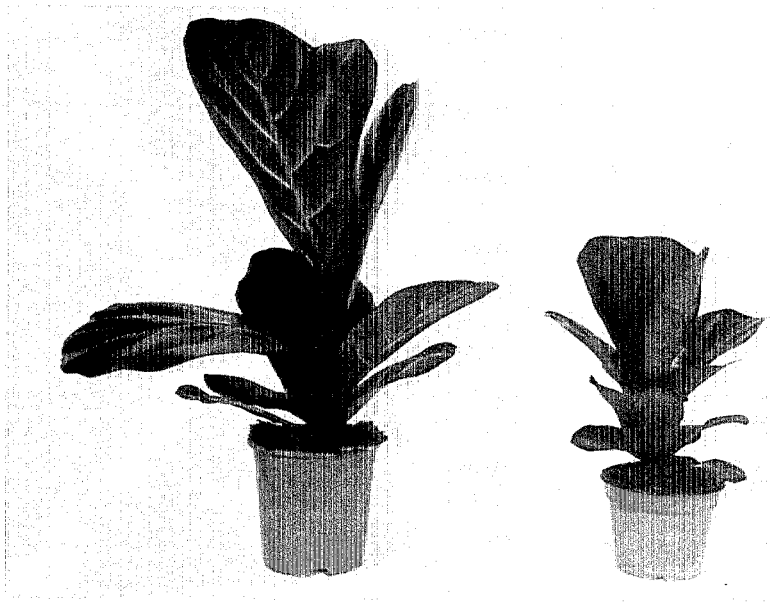
FIG. 2 illustrates for comparative purposes plants of the same age prepared from vegetative cuttings wherein the new Bambino cultivar is shown on the right and a typical *Ficus lyrata* plant is shown on the left. The disparity of growth habits is readily apparent.
Figure 3:
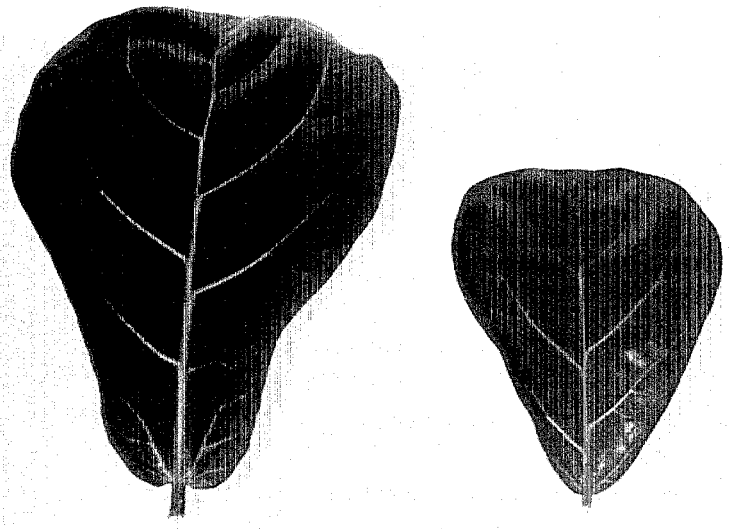

FIG. 3 illustrates for comparative purposes the upper surfaces of leaves wherein a leaf from the new Bambino cultivar is shown on the right and a leaf from a typical *Ficus lyrata* plant is shown in the left. Light venation is apparent on each leaf. The disparity in leaf sizes and shapes is apparent.

Figure 4:
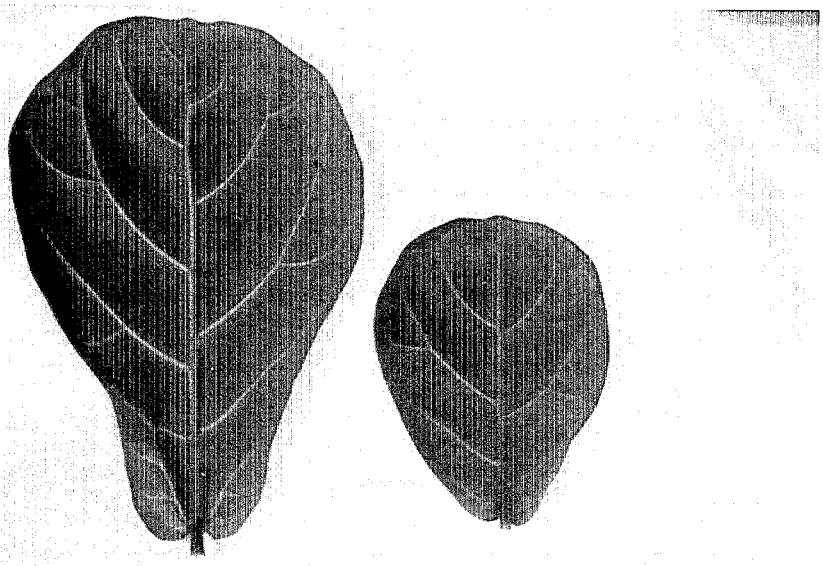

FIG. 4 illustrates for comparative purposes the lower surfaces of leaves wherein a leaf from the new Bambino cultivar is shown on the right and a leaf from a typical *Ficus lyrata* plant is shown on the left. Light venation apparent on each leaf. The disparity in leaf sizes and shapes is apparent.

DETAILED DESCRIPTION

The following observations, measurements and comparisons describe plants grown in greenhouses at Bleiswijk, The Netherlands. In the following description color references are made to the R.H.S. Colour Chart of The Royal Horitcultural Society, London, England.

Classification:

*Botanical.*—*Ficus lyrata,* cv. Bambino.

*Commercial.*—Fiddle-leaf fig.

Plant:

*Growth habit.*—Extremely compact (as illustrated).

Foliage: Color — Adaxial: Generally comparable to that of the species, somewhat darker than Yellow-Green Group 147A (as illustrated). Abaxial: Generally comparable to that of the species, approximately Yellow-Green Group 147B. Form — Broadly obovate and less fiddle-shaped than typically exhibited by the species. Venation — Visible and lighter in coloration on both leaf surfaces (as illustrated). Appearance — Attractive glossiness on adaxial surface.

*Size.*—Length: Commonly only approximately 14 to 21 cm. Width: Commonly only approximately 13 to 18 cm. at the widest point.

*Petioles.*—Commonly only approximately 1 cm. in length. This can be compared to a length of approximately 2 cm. for the typical *Ficus lyrata.*

*Internodes.*—Those of the main stem are very short and commonly are only approximately 2 cm. This can be compared to approximately 8 cm. for the typical *Ficus lyrata.*

*Stipules.*—Commonly are a dark blackish-brown that is nearly black in coloration. This can be compared to the reddish-brown coloration of the typical *Ficus lyrata.*

It will be apparent to members of the plant industry that the new Bambino cultivar can be grown to advantage as an attractive potted house plant particularly in those environments where space is limited. The distinctive character of the new cultivar readily distinguishes it from typical plants of the species and all previously known cultivars of the species.

I claim:

1. A new and distinct cultivar of *Ficus lyrata,* substantially as herein shown and described, having the following combination of characteristics:

(a) exhibits an extremely compact growth habit unlike that typically exhibited by *Ficus lyrata.*

(b) forms uniformly green leaves with light venation, (c) forms smaller and thicker leaves than are typically exhibited by *Ficus lyrata,* and (d) forms extremely short petioles that commonly are considerably longer in *Ficus lyrata.*

* * * * *

UNITED STATES PATENT AND TRADEMARK OFFICE

CERTIFICATE OF CORRECTION

PATENT NO. : PP 09,323
DATED : October 10, 1995
INVENTOR(S) : Eduard J.M. Van Der Knaap It is certified that error appears in the above-indentified patent and that said Letters Patent is hereby corrected as shown below:

Title page, item [54] the title should read--'BAMBINO'--.

Signed and Sealed this

Thirtieth Day of January, 1996

*Attest:*

*Attesting Officer*

BRUCE LEHMAN

*Commissioner of Patents and Trademarks*